United States Patent
Huxel et al.

(10) Patent No.: US 6,494,908 B1
(45) Date of Patent: *Dec. 17, 2002

(54) REMOVABLE STENT FOR BODY LUMENS

(75) Inventors: Shawn Thayer Huxel, Lawrenceville, NJ (US); Arindam Datta, Hillsborough, NJ (US); Yufu Li, Bridgewater, NJ (US); Dennis D. Jamiolkowski, Long Valley, NJ (US); E. Richard Skula, Wayne, NJ (US)

(73) Assignee: Ethicon, Inc., Somerville, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/470,620

(22) Filed: Dec. 22, 1999

(51) Int. Cl.[7] ................................................. A61F 2/06
(52) U.S. Cl. ...................... 623/1.22; 623/1.15; 623/1.46
(58) Field of Search ............................... 623/1.15–1.17, 623/1.18, 1.22, 1.21, 1.2, 1.19, 1.38, 1.44, 1.46, 1.47, 1.48, 1.49–1.54; 606/200, 194, 154, 151

(56) References Cited

U.S. PATENT DOCUMENTS

| | | |
|---|---|---|
| 4,741,337 A | 5/1988 | Smith et al. |
| 4,889,119 A | 12/1989 | Jamiolkowski et al. |
| 5,059,211 A | 10/1991 | Stack et al. |
| 5,160,341 A | 11/1992 | Brenneman et al. |
| 5,185,408 A | 2/1993 | Tang et al. |
| 5,346,501 A | 9/1994 | Regula et al. |
| 5,443,458 A | 8/1995 | Eury |
| 5,500,013 A * | 3/1996 | Buscemi et al. ............. 604/104 |
| 5,626,611 A | 5/1997 | Liu et al. |
| 5,728,135 A | 3/1998 | Bregen et al. |
| 5,792,400 A | 8/1998 | Talja et al. |
| 5,824,049 A | 10/1998 | Ragheb et al. |
| 5,873,904 A | 2/1999 | Ragheb et al. |
| 5,963,007 A | 10/1999 | Toyozawa et al. |
| 6,001,117 A | 12/1999 | Huxel et al. |
| 6,096,070 A | 8/2000 | Ragheb et al. |
| 6,117,168 A | 9/2000 | Yang et al. |
| 6,120,847 A | 9/2000 | Yang et al. |
| 6,153,252 A | 11/2000 | Hossainy et al. |
| 6,156,373 A | 12/2000 | Zhong et al. |
| 6,258,121 B1 | 7/2001 | Yang et al. |
| 6,338,739 B1 * | 1/2002 | Datta et al. ................. 623/1.15 |

FOREIGN PATENT DOCUMENTS

| | | | |
|---|---|---|---|
| EP | 0 523 743 A1 | 1/1993 | ............ A61L/17/00 |
| EP | 0 634 152 A1 | 1/1995 | .............. A61F/2/06 |
| WO | WO 90/04982 | 5/1990 | ............ A61L/27/00 |

* cited by examiner

Primary Examiner—Michael J. Milano
Assistant Examiner—(Jackie) Tan-Hyen T Ho
(74) Attorney, Agent, or Firm—Emil Richard Skula

(57) ABSTRACT

A removable stent for implantation into a lumen in a human body. The stent is made from a soft, flexible fiber having an outer surface. An outer bioabsorbable/degradable coating is applied to the outer surface of the filament causing it to become rigid. The coating softens in vivo through absorption and/or degradation such that the stent is readily passed or removed from the lumen as a softened filament after a pre-determined period of time through normal flow of body fluids passing through the lumen or by manual removal.

26 Claims, 8 Drawing Sheets

REMOVABLE STENT FOR BODY LUMENS

FIELD OF THE INVENTION

The field of art to which this invention relates is medical devices, in particular, removable stent devices having bioabsorbable or biodegradable polymer coatings.

BACKGROUND OF THE INVENTION

The use of stent medical devices, or other types of endoluminal mechanical support devices, to keep a duct, vessel or other body lumen open in the human body has developed into a primary therapy for lumen stenosis or obstruction. The use of stents in various surgical procedures has quickly become accepted as experience with stent devices accumulates, and the number of surgical procedures employing them increases as their advantages become more widely recognized. For example, it is known to use stents in body lumens in order to maintain open passageways such as the prostatic urethra, the esophagus, the biliary tract, intestines, and various coronary arteries and veins, as well as more remote cardiovascular vessels such as the femoral artery, etc. There are two types of stents that are presently utilized: permanent stents and temporary stents. A permanent stent is designed to be maintained in a body lumen for an indeterminate amount of time. Temporary stents are designed to be maintained in a body lumen for a limited period of time in order to maintain the patency of the body lumen, for example, after trauma to a lumen caused by a surgical procedure or an injury. Permanent stents are typically designed to provide long term support for damaged or traumatized wall tissues of the lumen. There are numerous conventional applications for permanent stents including cardiovascular, urological, gastrointestinal, and gynecological applications.

It is known that permanent stents, over time, become encapsulated and covered with endothelium tissues, for example, in cardiovascular applications. Similarly, permanent stents are known to become covered by epithelium, for example, in urethral applications. Temporary stents, on the other hand are designed to maintain the passageway of a lumen open for a specific, limited period of time, and preferably do not become incorporated into the walls of the lumen by tissue ingrowth or encapsulation. Temporary stents may advantageously be eliminated from body lumens after a predetermined, clinically appropriate period of time, for example, after the traumatized tissues of the lumen have healed and a stent is no longer needed to maintain the patency of the lumen. For example, temporary stents can be used as substitutes for in-dwelling catheters for applications in the treatment of prostatic obstruction or other urethral stricture diseases. Another indication for temporary stents in a body lumen is after energy ablation, such as laser or thermal ablation, or irradiation of prostatic tissue, in order to control post-operative acute urinary retention or other body fluid retention.

It is known in the art to make both permanent and temporary stents from various conventional, biocompatible metals. However, there are several disadvantages that may be associated with the use of metal stents. For example, it is known that the metal stents may become encrusted, encapsulated, epithelialized or ingrown with body tissue. The stents are known to migrate on occasion from their initial insertion location. Such stents are known to cause irritation to the surrounding tissues in a lumen. Also, since metals are typically much harder and stiffer than the surrounding tissues in a lumen, this may result in an anatomical or physiological mismatch, thereby damaging tissue or eliciting unwanted biologic responses. Although permanent metal stents are designed to be implanted for an indefinite period of time, it is sometimes necessary to remove permanent metal stents. For example, if there is a biological response-requiring surgical intervention, often the stent must be removed through a secondary procedure. If the metal stent is a temporary stent, it will also have to be removed after a clinically appropriate period of time. Regardless of whether the metal stent is categorized as permanent or temporary, if the stent has been encapsulated, epithelialized, etc., the surgical removal of the stent will resultingly cause undesirable pain and discomfort to the patient and possibly additional trauma to the lumen tissue. In addition to the pain and discomfort, the patient must be subjected to an additional time consuming and complicated surgical procedure with the attendant risks of surgery, in order to remove the metal stent.

Similar complications and problems, as in the case of metal stents, may well result when using permanent stents made from non-absorbable biocompatible polymer or polymer-composites although these materials may offer certain benefits such as reduction in stiffness.

It is known to use bioabsorbable and biodegradable materials for manufacturing temporary stents. The conventional bioabsorbable or bioresorbable materials from which such stents are made are selected to absorb or degrade over time, thereby eliminating the need for subsequent surgical procedures to remove the stent from the body lumen. In addition to the advantages attendant with not having to surgically remove such stents, it is known that bioabsorbable and biodegradable materials tend to have excellent biocompatibility characteristics, especially in comparison to conventionally used biocompatible metals in certain sensitive patients. Another advantage of stents made from bioabsorbable and biodegradable materials is that the mechanical properties can be designed to substantially eliminate or reduce the stiffness and hardness that is often associated with metal stents, which can contribute to the propensity of a stent to damage a vessel or lumen.

However, there are disadvantages and limitations known to be associated with the use of bioabsorbable or biodegradable stents. The limitations arise from the characteristics of the materials from which such stents are made. One of the problems associated with the current stents is that the materials break down too quickly. This improper breakdown or degradation of a stent into large, rigid fragments in the interior of a lumen, such as the urethra, may cause obstruction to normal flow, such as voiding, thereby interfering with the primary purpose of the stent in providing lumen patency. Alternatively, they take a long time to breakdown and stay in the target lumen for a considerable period of time after their therapeutic use has been accomplished. There is thus a long-term risk associated with these materials to form stones when uretheral stents made from longer degrading biodegradable polymers.

Accordingly, there is a need in this art for novel, temporary stents, wherein the stents remain functional in a body lumen for the duration of a prescribed, clinically appropriate period of time to accomplish the appropriate therapeutical purpose, and, then soften and are removable as an elongated string-like member without producing fragments, which may cause irritation, obstruction, pain or discomfort to the patient, and without the need for a surgical procedure.

In a preferred embodiment of the present invention, the temporary stent readily passes out of the body, or is removed as, a limp, flexible string-like member, and irritation, obstruction, pain or discomfort to the patient is either eliminated, or if present, is minimal.

SUMMARY OF THE INVENTION

It is an object of the present invention to provide a stent for insertion into a body lumen which is manufactured from a flexible filament member, such as a suture, and then coated with a biodegradable or bioabsorbale polymer such that the member is formed into a relatively rigid stent, and when in the body, softens back into a flexible filament member which is easily passed or removed from the body lumen after a specific therapeutic period of time.

Therefore, an implantable stent is disclosed for use in body lumens, wherein such lumens exist as part of the natural anatomy or are made surgically. The stent is an elongate, hollow member having a helical or coiled structure, and in a preferred embodiment has a helical structure having a plurality of coils. The structure has a longitudinal axis and a longitudinal passage. The coils have a pitch. The structure is made from a flexible, limp filament or fiber, such as a surgical suture, having an exterior polymeric coating. The polymeric coating is a bioabsorbable or biodegradable polymer, or blend thereof. At body temperature, the coating is solid, and of sufficient thickness to effectively cause the flexible, limp member to be maintained in a substantially rigid, fixed state as a structure. The rate of degradation or absorption of the coating in vivo is sufficient to effectively soften or be removed from the outer surface of the filament within the desired therapeutic period. This effectively provides that as the coating degrades, softens or is absorbed in vivo, it loses its mechanical integrity. This allows the filament to revert to its natural, flexible limp state, causing the stent structure to effectively collapse, and the filament may be removed or eliminated from the lumen.

Upon in vivo exposure to body fluids, the progressively degrading and/or absorbing coating causes the stent to soften and collapse into a flexible filament that can readily pass out of the body lumen, either by manipulation or through natural expulsion with body fluids, thereby minimizing the possibility of causing obstruction, pain or discomfort.

Yet another aspect of the present invention is the above-described stent made from a fiber which is radio-opaque.

Yet another aspect of the present invention is a method of using the stents of the present invention in a surgical procedure to maintain the patency of a body lumen. A stent of the present invention is provided. The stent is an elongate, hollow member and in a preferred embodiment has a helical structure having a plurality of coils. The member has a longitudinal axis. The coils have a pitch. The structure is made from a flexible, limp filament or a fiber, having an outer surface and an exterior polymeric coating. The stent is inserted into a body lumen. The exposure to in vivo body fluids causes the exterior coating to absorb and/or degrade and soften, thereby causing the stent structure to collapse and return to a limp, flexible filament that can then be either eliminated by the passage of body fluids or manually removed.

These and other aspects of the present invention will become more apparent from the following description and examples, and accompanying drawings.

DESCRIPTION OF THE PREFERRED EMBODIMENTS

Figure 1:
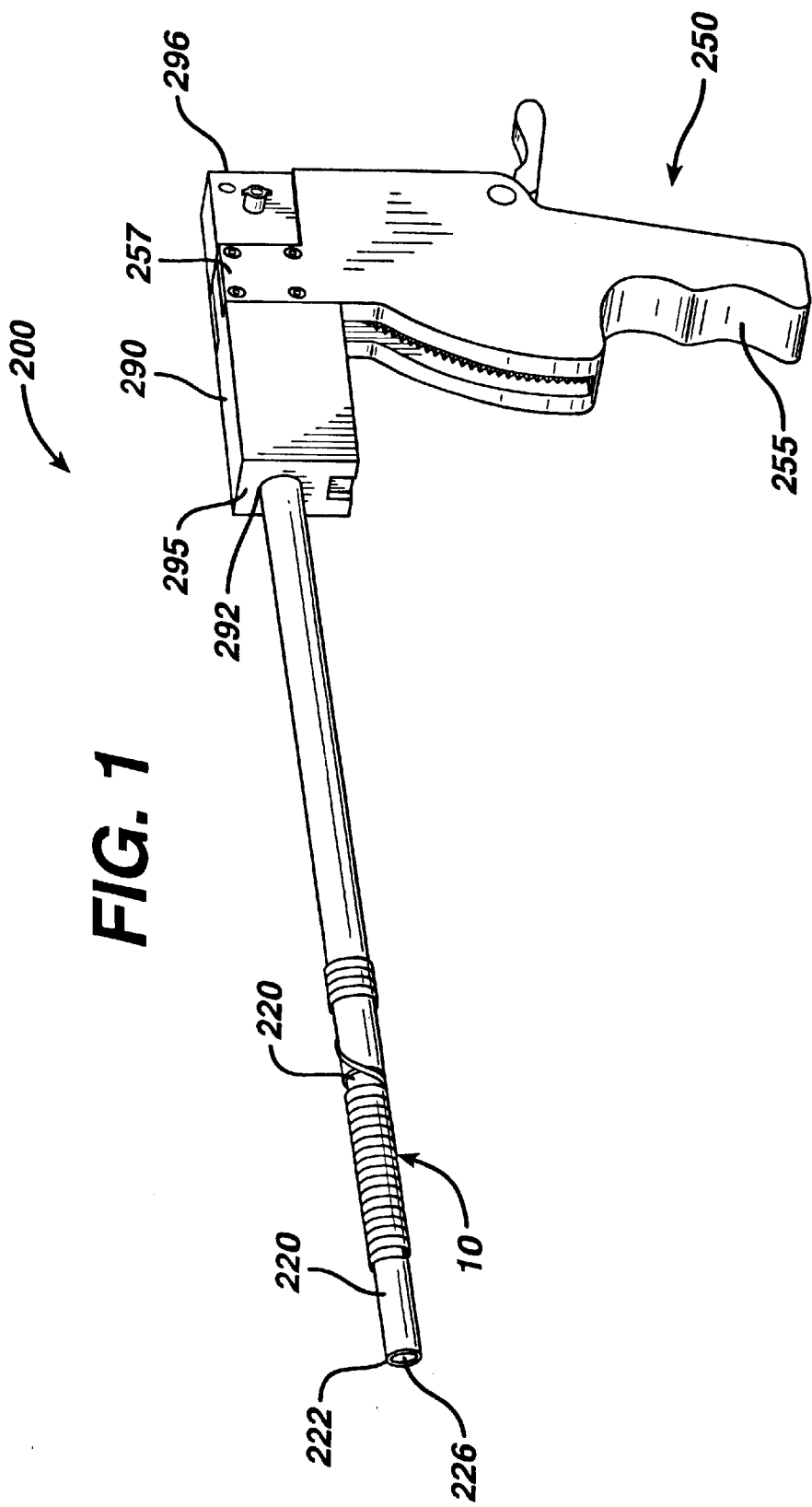
FIG. 1 is a perspective view of a preferred embodiment of a stent device of the present invention mounted to the distal end of an applicator instrument.
Figure 2:
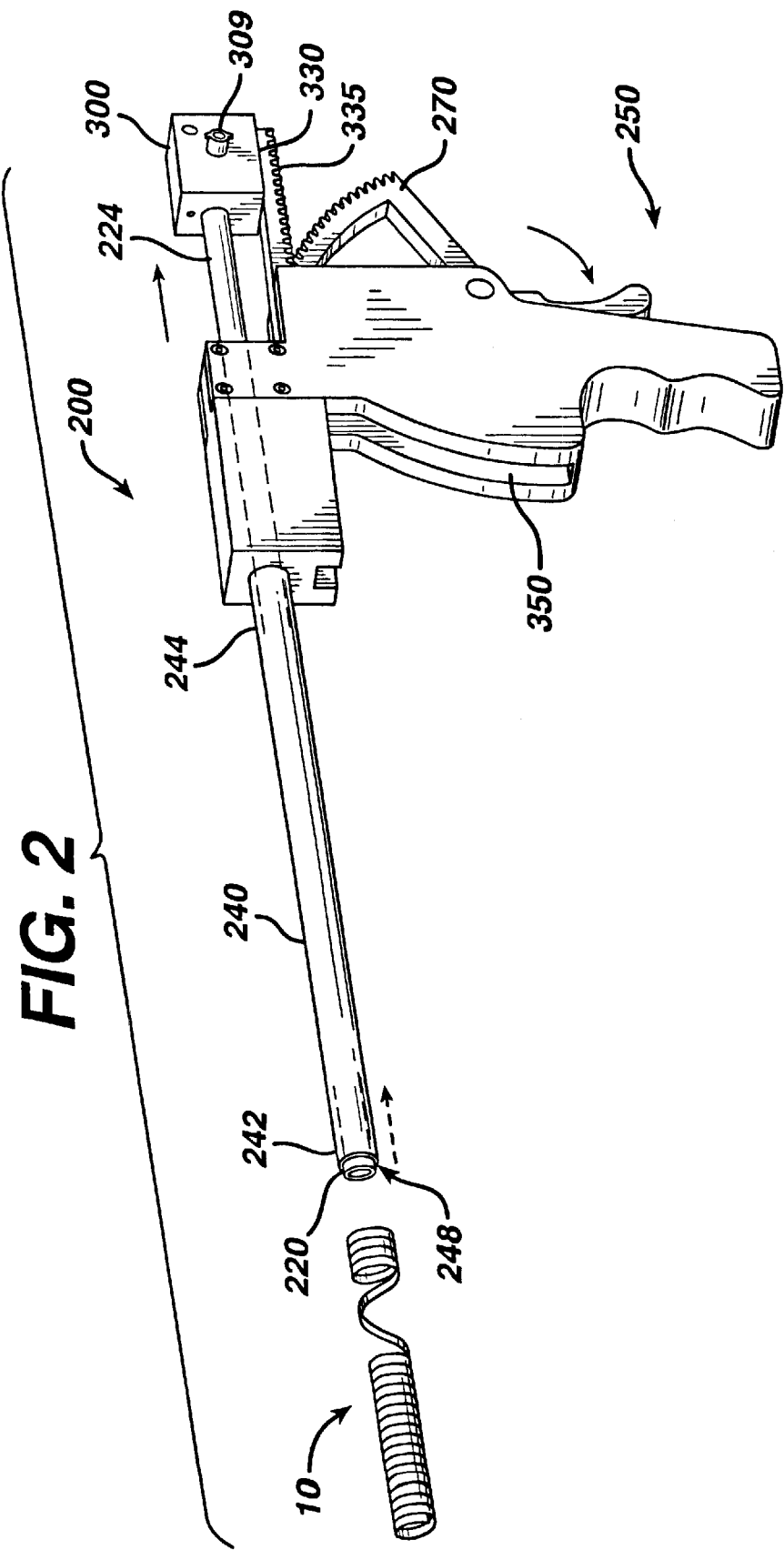
FIG. 2 is a perspective view of the stent and applicator of FIG. 1, prior to loading the stent onto the applicator instrument.
Figure 3:
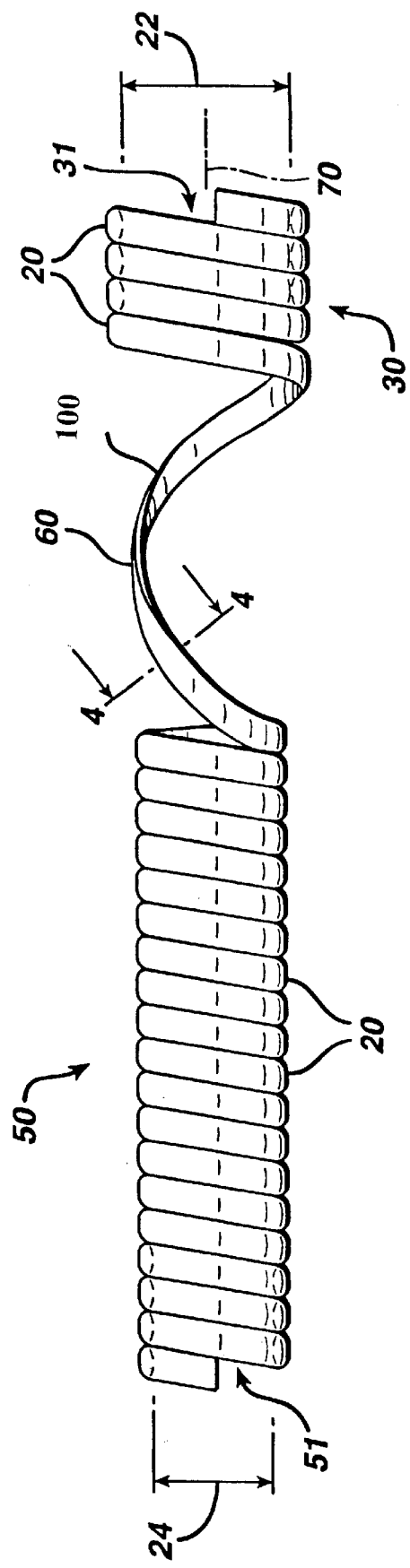
FIG. 3 is a side view of a stent device of the present invention, having a helical configuration.
Figure 4:
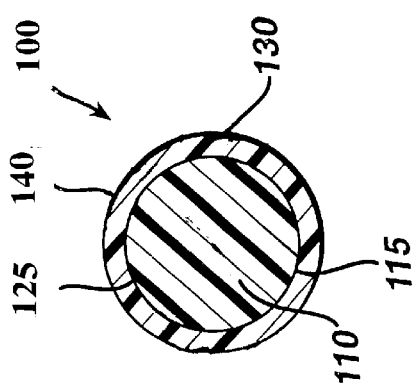
FIG. 4 is a cross-sectional view of the fiber used to make the stent of FIG. 3 taken along View Line 4—4 illustrating a circular cross-section.
Figure 5:
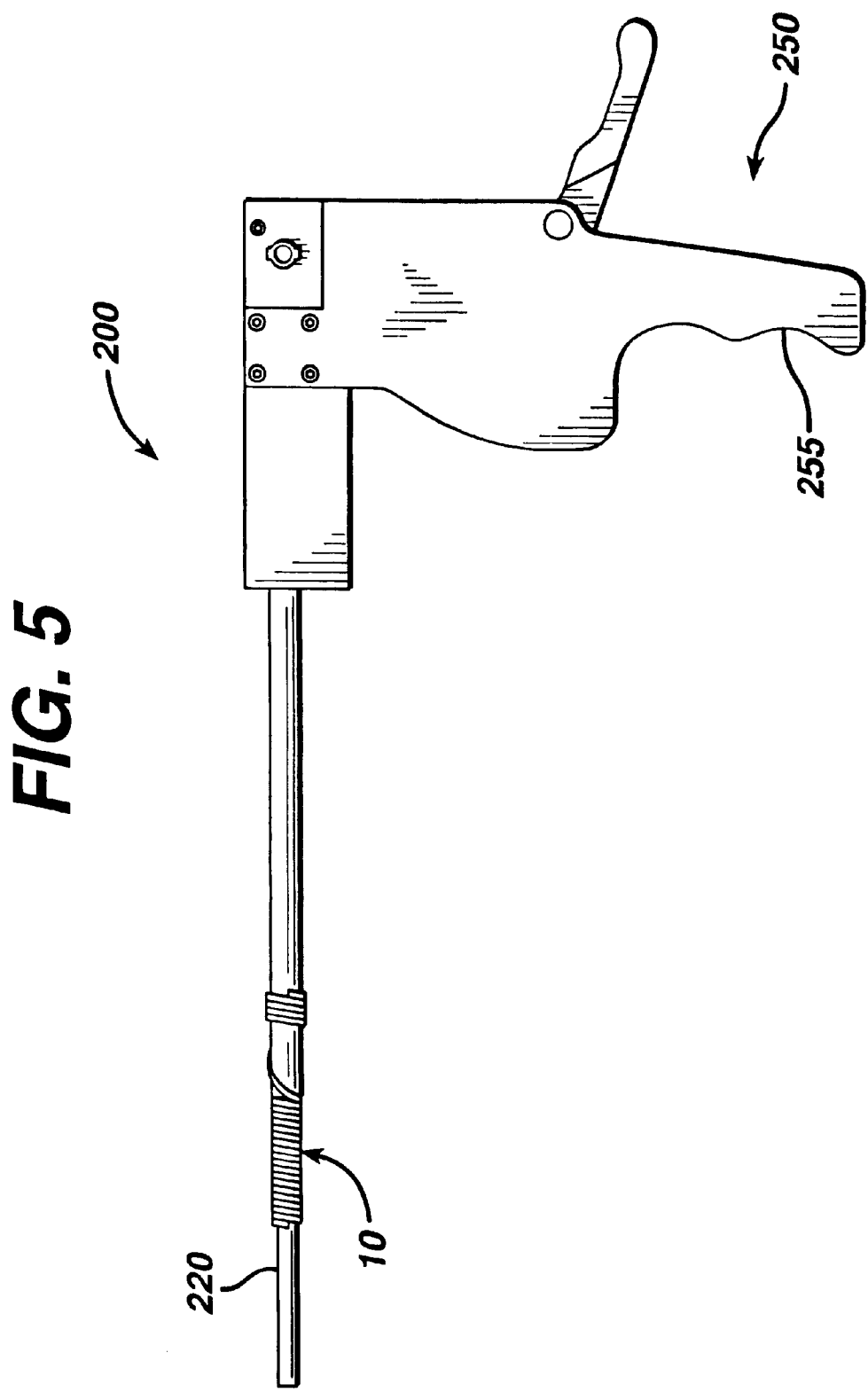
FIG. 5 is a side view of the stent and applicator device of FIG. 1, where the device is shown in the ready position, prior to application.
Figure 6:
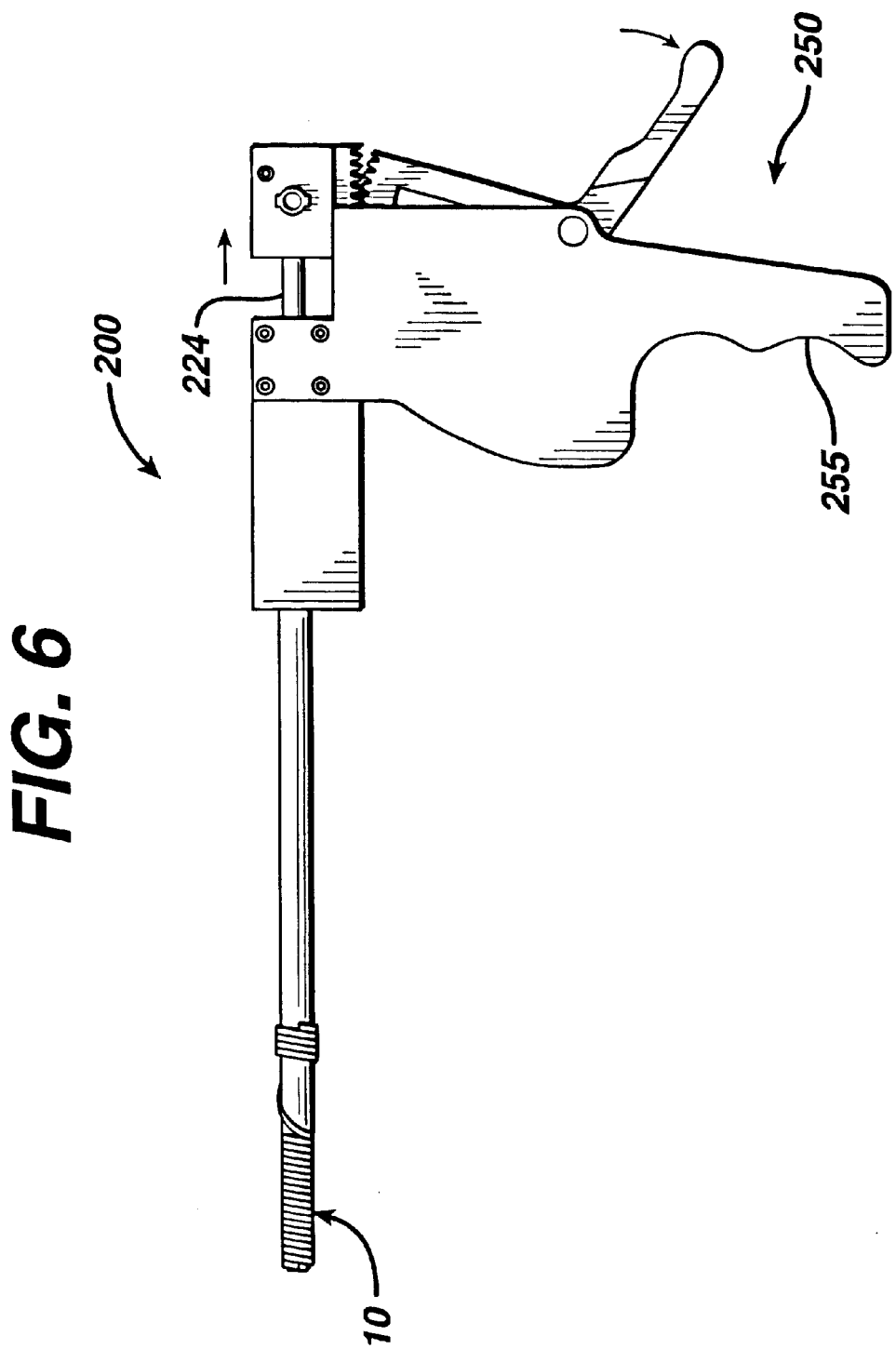
FIG. 6 is a side view of the stent and applicator device of FIG. 5, illustrating the position of the stent relative to the applicator when the stent is partially deployed by engaging the applicator trigger.
Figure 7:
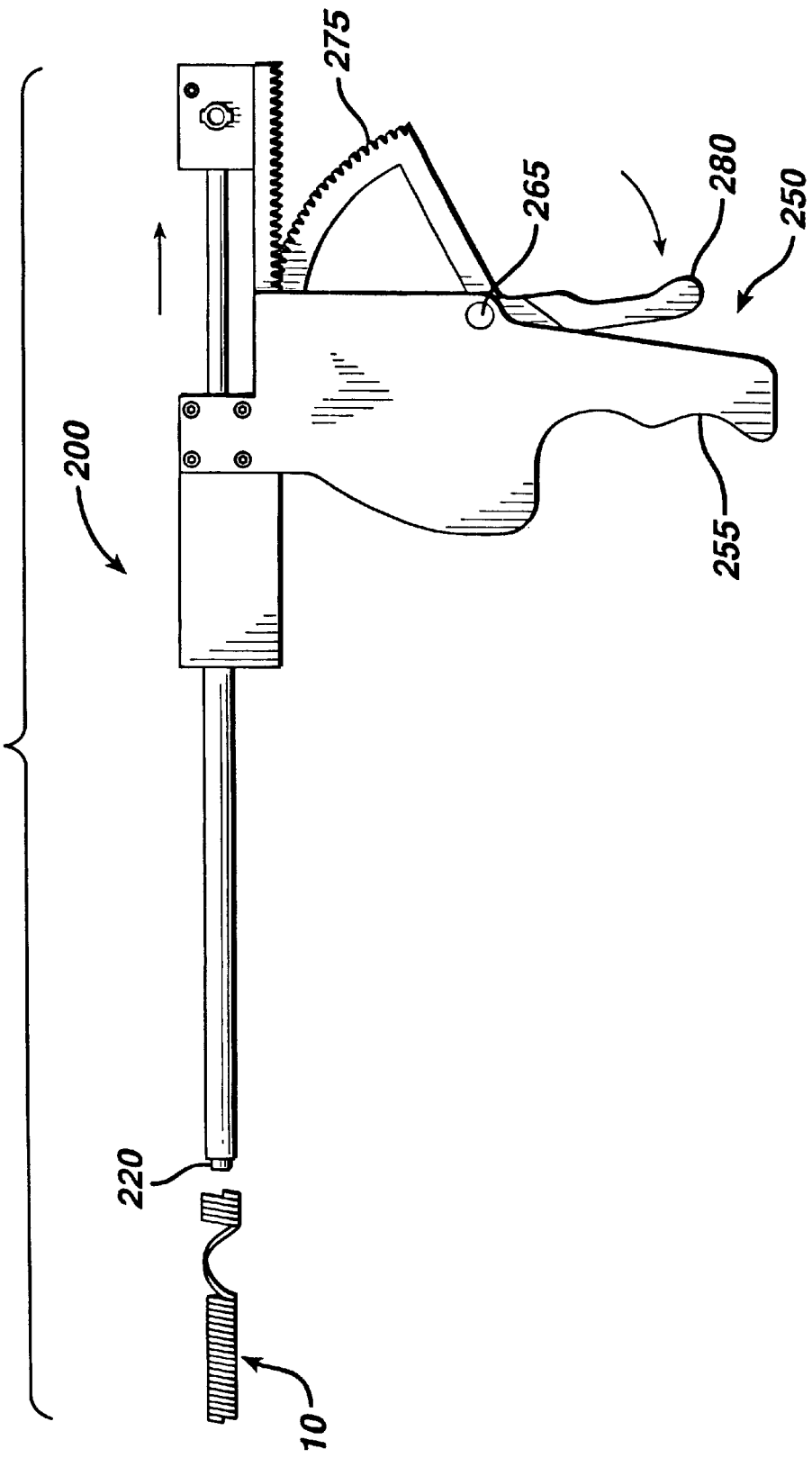
FIG. 7 illustrates the relative positions of the stent to the applicator of FIG. 6 when the stent is fully deployed by fully engaging the applicator trigger.

Referring to FIGS. 1–9, a preferred embodiment of a stent of the present invention is illustrated. As seen in FIG. 3, the stent 10 is seen to be a helical structure having a series of connected coils 20. The coils are made from filament 100. The term filament as used herein is defined to include not only filaments but fibers as well, and is used interchangeably with the term fiber. It is preferred that filament 100 be a continuous filament, however, it is possible to make stent 10 from two or more sections of filament which are subsequently connected or hinged together. As seen in FIG. 4, the filament 100 is seen to have inner flexible member 110 and outer coating 130. The inner flexible member 110 is seen to have outer surface 115. Covering the outer surface 115 of flexible member 110 is the outer coating 130. Outer coating 130 is seen to have inner surface 135 and exterior surface 140. Preferably, inner surface 135 is in contact with, and affixed to, the outer surface 115. The stent is seen to have a longitudinal axis 70, and internal passageway 11. The stent 10 is seen to have a first distal section 30 of coils 20 connected to a second section 50 of coils 20, wherein the sections 30 and 50 are connected by hinged connecting fiber 60. The distal section 30 of coils adjacent to hinged connecting fiber 60 forms an anchoring section which is inserted distal to the external sphincter. The proximal section 50 of the stent 10 is maintained within the prostatic urethra. Proximal section 50 is seen to have coils 20 having diameter 24, and also has passageway 51. The distal section 30 of stent 10 has coils 20 having a diameter 22. Distal section 30 also has a passageway 31. Passage ways 31 and 51 are in communication to form passageway 11 of stent 10. As seen in FIG. 4, one preferred embodiment of the stent 10 of the present invention has a filament 100 having a circular cross-sectional configuration. The filament 100 may have various configurations depending upon the application including round, square, polygonal, curved, oval, and combinations thereof and equivalents thereof. Those skilled in the art will appreciate that certain cross-sectional configurations will provide different advantages in the stent. For example, the advantages of fiber of the present invention having a round cross-section include ease of the stent manufacturing process due to a possible on-line, one-step transition from the fiber to the stent in future manufacturing processes, flexibility during the stent deployment by being able to tailor the length of the stent during a surgical procedure to fit a particular patient's anatomy, and the use of commercially available filaments such as sutures.

The stent 10 is preferably manufactured from a flexible, polymeric filament 100 having a desired cross-sectional configuration. The length and overall diameter of the stent 10 will depend upon a number of factors including the anatomy of the patient, the size of the anatomy and the type of surgical procedure which has effected the urethral lumen. For example, the overall length of a stent 10 useful in the practice of the present invention will be sufficient to effectively maintain the lumen passage open. Typically the length for urethral applications in and adult male, the length will be about 10 mm to about 200 mm, more typically about 20 mm to about 100 mm, and preferably about 40 mm to about 80 mm. The diameter of a stent 10 of the present invention will be sufficient to effectively maintain patency of the lumen. For prostatic urethral applications, where the stent has two sections having different diameters, typically the diameter in the prostatic urethra will typically be about 2 mm to about 25 mm, more typically about 4 mm to about 15 mm, and preferably about 6 mm to about 10 mm. The diameter of the section used to anchor distal to the external sphincter will be about 2 mm to about 25 mm, more typically about 4 mm to about 15 mm, and preferably about 6 mm to about 10 mm. The major cross-sectional dimension of a fiber used to manufacture a stent of the present invention will be sufficient to provide effective support and flexibility. Typically, when utilizing a circular cross-section, the diameter for urethral applications will be about 0.1 mm to about 4 mm, more typically about 0.5 mm to about 3 mm, and preferably about 1 mm to about 2 mm. The pitch, length, diameter and fiber diameter of the stents of the present invention will be sufficient to effectively provide sufficient support in response to radial stress of the urethral vessel walls, while providing for ease of insertion and stability while inserted in the urethral lumen, as well as desired flexibility and lumen patency. The pitch of the stent is defined to be the number of coils per unit length. In this patent application specification, for this example, pitch is defined as the number of coils per centimeter of stent length. Typically, for urethral applications, the pitch will be about 2.5 to about 100, more typically about 3 to about 20, and preferably about 5 to about 10. Although it is preferred for urethral applications that there be no space between adjacent coils, the stents of the present invention may have spaces between adjacent coils.

The flexible members 110 coated with coatings 130 to form filaments 100 of the present invention will preferably be selected to have sufficient flexibility and softness and limpness to effectively provide for a stent that will collapse and be easily removed from a body lumen. The materials useful for the flexible member include flexible, limp monofilament and braided string-like members. It is particularly preferred to use conventional nonabsorbable sutures, such as monofilament or braided polypropylene, silk, polyester, nylon and the like and equivalents thereof. The flexible members may also be conventional absorbable sutures, monofilament or braided, including 95/5 lactide/glycolide, and polydioxanone, and the like. The flexible member 110 may also be made from yarn type materials made from biocompatible fibers that are "spun" together to form the yarn.

The outer coatings useful for the stents and filaments of the present invention will be conventional biodegradable or bioabsorbable polymers, and blends thereof, including polymers made from monomers selected from the group consisting of lactide, glycolide, para-dioxanone, caprolactone, and trimethylene carbonate, caprolactone, blends thereof and copolymers thereof. The effect of the degradation or absorption of the polymeric coating is to convert the filament back into a soft, flexible member after a predetermined time period, such that the stent effectively collapses, and the flexible member can then be easily removed or passed from the lumen. In a flow environment, the progressively degrading stent can readily pass through the body or be removed from the lumen without causing obstruction. The types of polymeric coatings that can advantageously provide stiffness to form a filament 100 include polymers with glass transition temperatures above room temperature and preferably above 55° C., and most preferably above about 120° C. These materials may be amorphous, that is, not display crystallinity. Polymers that have glass transition temperatures that are low, especially below room temperature, will generally require some crystallinity to provide the dimensional stability and stiffness to function in the present application. These can be described as semicrystalline. Regarding water soluble polymers for the coating, there are two general classes of water soluble polymers: ionic and non-ionic. In general of use are polyacrylamides, polyacrylic acid polymers, polyethers (especially the polyethylene glycols or polyethylene oxides), vinyl polymers such as some polyvinyl alcohols and some poly(N-vinyl pyrrolidone)s. Certain polysaccharide gums may also be useful; certain hydroxy celluloses, such as hydroxy methyl cellulose or certain hydroxy isopropyl cellulose are also useful.

One can control the dissolution process by material selection. Altering molecular weight of the water soluble resin also provides a means of control. One can control the dissolution process by material selection. Altering molecular weight of the water soluble resin also provides a means of control.

Utilization of polymer blending is particularly advantageous to achieve the necessary rates of dissolution. Polyamide (nylon) may be used as a component to advantage because it can provide mechanical strength, absorbs some water, etc.

A possible preferred blend component is polyethylene glycol (PEG or polyethylene oxide, PEO), especially those higher molecular weight resins that are semicrystalline. The melting point of PEG is about 60° C., which is high enough to meet requirements of a coating useful in the present invention. Optionally, the PEO may be blended with nylon. In addition, biodegradable polymers made from poly glycolide/lactide copolymers, polycaprolactone, and the like may be used for the outer coating of the filament 100. In addition, polyoxaesters can be utilized which are water soluble and degrade by hydrolysis. Other suitable polymers are found in U.S. Pat. No. 5,980,551, which is incorporated by reference.

A stent must be designed to withstand radial stresses in order to perform its function of maintaining a passage through a lumen open. The mechanical capability of the stents of the present invention to withstand radial stresses when the stent is emplaced in the body lumen is provided primarily by the biodegradable/bioabsorbable material in the outer coating. The strength and stiffness and thickness of this material in the outer coating is sufficient to be effectively withstand the loads necessary to keep the stent functional. As the coating degrades and breaks down, it will have a sufficient thickness of properly selected biodegradable material to effectively be able to withstand the load necessary for the time period required to keep the lumen patent. In essence then, the coating can be designed to fulfill the mechanical requirements of keeping the body lumen patent or open for the specific therapeutic time period.

After the coating has degraded/absorbed and effectively been removed from the stent structure by body fluids, the remaining filament returns to its soft, pliable, fibrillar state as a flexible member. The remaining soft filament is readily excreted or removed from the lumen.

The coated filaments of the present invention may be made by conventional processes including co-extrusion, melt coating, solution coating or powder coating followed by spreading the coating by melting, etc., and the like. For example, when using a coating process, the inner flexible member can be a mono-filament extruded material or can be made from a multi-filament braid. The outer coating can be added on top of the flexible member either by melt coating or solution coating by passing the inner core through a bath, through coating rollers, brushes, spraying and/or a die.

In another embodiment of the present invention, the polymers and blends that are used to form the coating can be used as a drug delivery matrix. To form this matrix, the coating material would be mixed with a therapeutic agent. The variety of different therapeutic agents that can be used in conjunction with the polymers of the present invention is vast. In general, therapeutic agents which may be administered via the pharmaceutical compositions of the invention include, without limitation: anti-infectives such as antibiotics and anti-viral agents; analgesics and analgesic combinations; anti-inflammatory agents; hormones such as steroids; bone regenerating growth factors; and naturally derived or genetically engineered proteins, polysaccharides, glycoproteins, or lipoproteins.

Matrix formulations may be formulated by mixing one or more therapeutic agents with the polymer. The therapeutic agent, may be present as a liquid, a finely divided solid, or any other appropriate physical form. Typically, but optionally, the matrix will include one or more additives, such as diluents, carriers, excipients, stabilizers or the like.

The amount of therapeutic agent will depend on the particular drug being employed and medical condition being treated. Typically, the amount of drug represents about 0.001 percent to about 70 percent, more typically about 0.001 percent to about 50 percent, most typically about 0.001 percent to about 20 percent by weight of the matrix. The quantity and type of polymer incorporated into the drug delivery matrix will vary depending on the release profile desired and the amount of drug employed.

Upon contact with body fluids, the polymer coating undergoes gradual degradation (mainly through hydrolysis) or absorption with concomitant release of the dispersed drug for a sustained or extended period. This can result in prolonged delivery (over, say 1 to 5,000 hours, preferably 2 to 800 hours) of effective amounts (say, 0.0001 mg/kg/hour to 10 mg/kg/hour) of the drug. This dosage form can be administered as is necessary depending on the subject being treated, the severity of the affliction, the judgment of the prescribing physician, and the like. Following this or similar procedures, those skilled in the art will be able to prepare a variety of formulations.

The stents 10 of the present invention when made from the coated filament 100 may be manufactured in the following manner using a winding process. A filament 100 is wound about a mandrel by heating the filament 100 and then coiling it around the mandrel. The assembly of the mandrel and the coil are annealed under constraint and then the mandrel is removed. The pitch and diameter of the coils are selected to provide the desired size and shape of stent. If desired, the filament 100 may be wound about the mandrel without heat, for example immediately upon entering a coating bath or melt bath, or the uncoated flexible member 110 can be wound about a mandrel, and then the coating can be applied in a conventional manner, and cured as necessary.

The stents of the present invention may be utilized in the following manner in urethral stent placement procedures as illustrated in FIGS. 1, 2, 5, 6, 7 and 8. Initially a stent 10 is placed upon the distal end of an applicator instrument 200. Instrument 200 is seen to have handle 250 having grip 255. At the top 257 of the handle 250 is mounted the shaft retention member 290. Retention member 290 is seen to have longitudinal passageway 292, front 295 and back 296. The mounting tube 240 is seen to have distal end 242 and proximal end 244. Mounting tube 240 is seen to have passage 248. The proximal end 244 of tube 240 is seen to be mounted in passage way 292 such that the inner passageway 248 is in communication with passageway 292. Slidably mounted in passageway 248 is the applicator tube 220. Tube 220 has distal end 222, proximal end 224, and passageway 226. Mounted to the proximal end 224 of tube 220 is the mounting block 300, which is affixed to end 224 by pin 309. Mounted to the bottom of block 300 is rack gear member 330 having gear teeth 335. Contained in handle 250 is the cavity 350 for receiving pinion gear member 270, having teeth 275. Pinion gear member 270 is pivotally mounted in cavity 350 by pivot pins 265. Teeth 275 mesh with and are engaged by teeth 335. Extending out from pinion gear member 270 on the opposite side of pins 265 is the actuation trigger 280. Actuation of trigger 280 will move tube 220 proximally and distally with respect to tube 240. Actuating the trigger 280 will allow the stent 10 to be released from the tubes 220 and 240.

Figure 8:
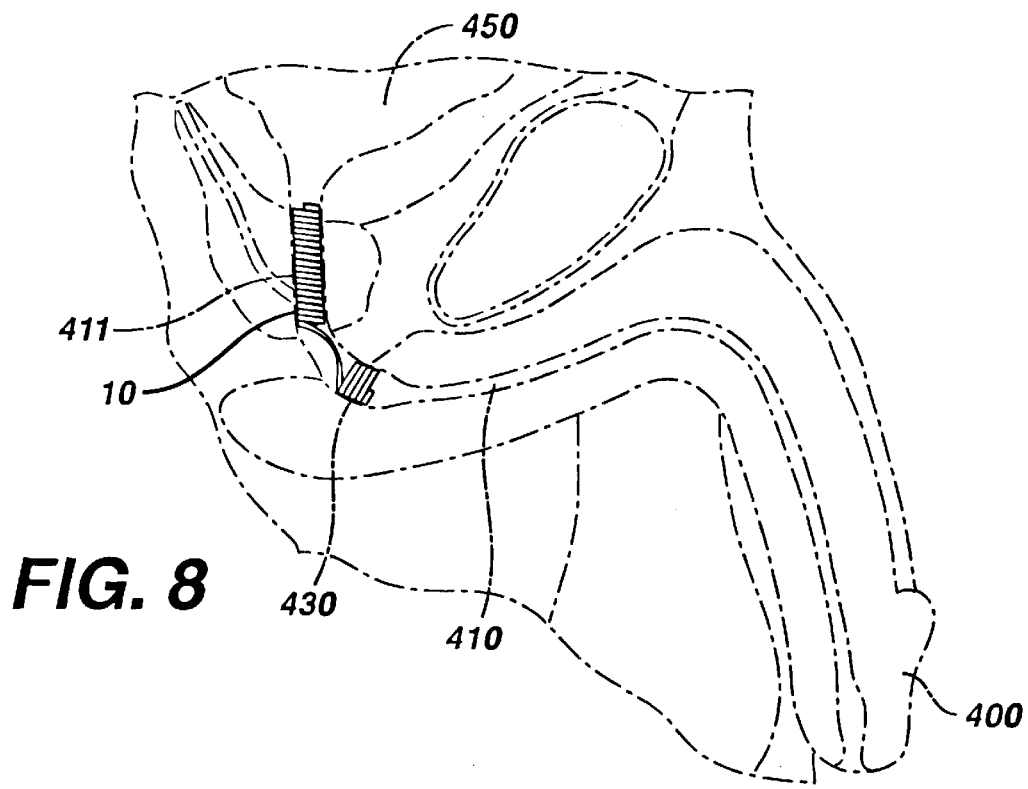
FIG. 8 illustrates the stent of the present invention fully deployed in the urethra and prostate of a patient, providing for a patent lumen.
Figure 9:
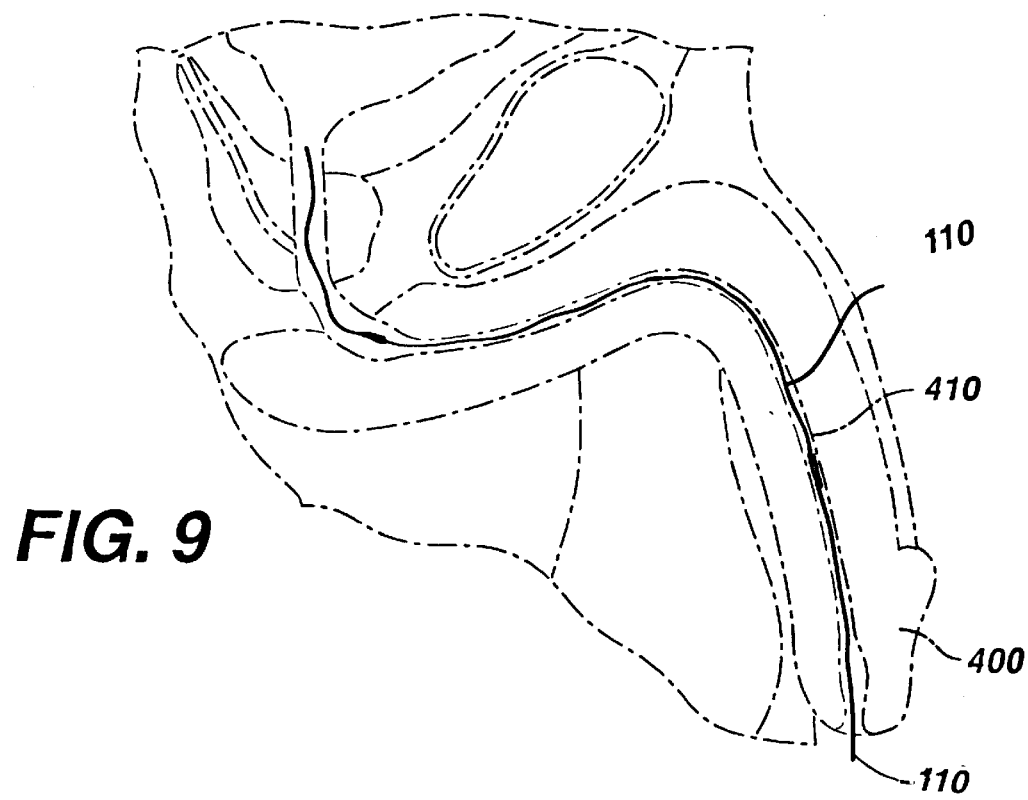
FIG. 9 illustrates a stent of the present invention emplaced in the urethra of a patient after the coating has degraded, been absorbed or otherwise broken down or softened; showing the stent being removed from the body as an elongated, soft, flexible filament.

The stent and distal end of the instrument 200 are inserted into the urethra 410 through the meatus 400 of the patient's penis as seen in FIGS. 8 and 9. The distal end of the instrument 200 and the stent 10 are manipulated through the urethra 410 such that the prostatic section of the stent is located within the prostatic urethra 411 and the distal end of the stent is distal to the external sphincter 430, thereby providing an open passage for urine from bladder 450 through the lumen of the urethra. Then, the application instrument 200 is withdrawn from the urethra 410 by engaging trigger 260 and pulling distally on the instrument, thereby completing the procedure and providing for an implanted stent 10 which allows for patency of the urethral lumen 410. As seen in FIG. 9, the stent 10 after having been in place for the appropriate period of time has been converted into a state wherein it is substantially a soft, flexible filament, and is readily passed from the urethra 410 out of the patient's body with the urine flow, or is manually pulled out of the lumen. It will be appreciated by those skilled in the art that placement for other types of body lumens could be done in a similar manner, with modification as required by the unique characteristics of the lumen or of the surgical emplacement procedure.

The following examples are illustrative of the principles and practice of the present invention, although not limited thereto.

EXAMPLE 1

Manufacture of filament having absorbable coating by extrusion coating process.

A polydioxanone homopolymer was added to a nitrogen purged hopper of a ¾" vertical single screw extruder with a 24:1 L:D standard screw. The temperature profile of the extruder was 250°, 260°, 270° and 275° F. from rear zone to die. The screw speed was 6.5 RPM and the adapt pressure was 1345 psi. A B&H 25 cross head was employed with a 20 mil diameter guider (pressure tip) and a 48 mil diameter die. A spool of Vicryl brand suture, available from Ethicon, Inc., Somerville, N.J., with 18 mil diameter on a pay-off was guided through the guider inside the cross head, then coated by polydioxanone molt, chilled in a water trough, dried by a air wiper, took off and spooled sequentially. The temperature of the water trough was 8° C. The take-off speed was 2.1 M/min. The fiber with the O.D. of 44 mil was made and stored in nitrogen environment.

EXAMPLE 2

Figure 10:
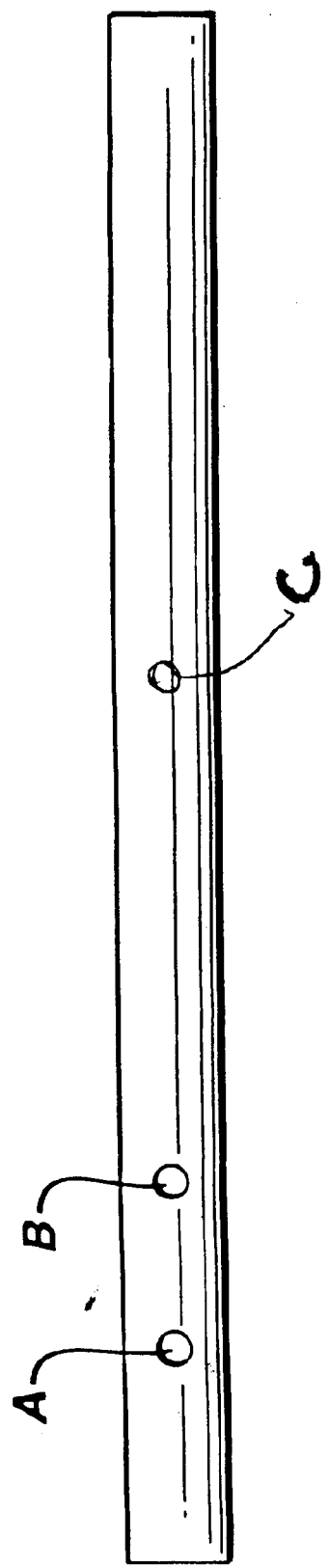
FIG. 10 is a schematic of a mandrel used to manufacture stents in Example 3.

Manufacture of stent using the coated filament The coated suture of Example 1 was tied so that it created a small loop through the first hole C of the mandrel (see FIG. 10). Two metal posts (φ2×15 mm length) are inserted into the holes A and B.

A post was located at hole A and B. Clamp the C-side end of the mandrel to a winding motor. The 5-foot long fiber was cut from the spool and passed through the loop. The two free ends were held together and the folded fiber was stretched loosely so that the loop was positioned to be in the approximate center of the fiber. The fiber was loosely hold by two figures as a guide to make sure that the coils are packed closely together. A winder was run between 20–30 RPM for the length of the Prostatic Section.

The coiling start from point C. Once the first post (B) was reached, the fiber was then bent over the post at an angle toward the distal section. Winding 180° more to form the connector, the fiber reached toward the second post (A), and then past it. The fiber is pulled back to a perpendicular position to the mandrel and the distal loop is then coiled. A wire tie was used to secure the fiber onto the mandrel. The assembly was stored under vacuum for 48 hours to allow it to dry prior to annealing.

Prior to annealing, the posts were removed from the mandrel. The entire assembly was hanged in annealing over and annealed at 80° C. for 10 hours. The stent was removed from the mandrel and stored in nitrogen box.

EXAMPLE 3

A male patient is appropriately anesthetized and undergoes a prostrate thermal ablation procedure using conventional laser treatment devices. After successful completion of the surgical procedure, a stent 10 of the present invention is inserted into the patient's urethra and bladder in the following manner using an applicator 200. The surgeon trims the stent to size. The stent is placed at the end of the applicator. A conventional scope is inserted into the lumen of the applicator. The stent and applicator are lubricated with a water soluble medical grade lubricant. A fluid reservoir is attached to the applier as in any standard cystoscopy procedure. The stent is placed in the prostatic urethra under direct visualization using a scope. Once positioned correctly, the applier is removed, leaving behind the stent in the prostatic urethra. In approximately 28 days after implantation, the outer coating absorbs and or degrades, thereby converting the stent into a soft, flexible filamentary structure that is removed from the urinary tract by grasping the end of the filament and pulling it from the lumen.

The stents of the present invention provide many advantages over the stents of the prior art. The advantages include: rigidity (lumen patency) for a prescribed time; a degradation/absorption softening mechanism, whereby the stent softens into a readily passable/removable filament; biocompatibility; means to prevent migration; means to non-invasively monitor the stent and its position by X-ray. etc.

Although this invention has been shown and described with respect to detailed embodiments thereof, it will be understood by those skilled in the art that various changes in form and detail may be made without departing from the spirit and scope of the claimed invention.

We claim:

1. A stent, comprising:
    a helical structure having a plurality of coils, said structure having a longitudinal axis and said coils having a pitch, said structure having an internal longitudinal passage wherein said structure is made from a filament having a cross-section and an outer surface, said filament comprising:
    a soft flexible elongated member having an outer surface; and
    a bioabsorbable or biodegradable polymeric outer coating on the outer surface of the member;
    wherein, the polymeric coating has sufficient mechanical integrity to effectively maintain the flexible member in a helical configuration, until the coating has sufficiently been degraded or absorbed in vivo to effectively convert the helical structure back into a soft, elongated member.

2. The stent of claim 1 wherein the coating comprises a melt polymer.

3. The stent of claim 1, wherein the coating comprises a solution polymer.

4. The stent of claim 1 wherein the filament comprises a surgical suture.

5. The stent of claim 4, wherein the suture comprises a monofilament.

6. The stent of claim 4, wherein the suture comprises a multifilament.

7. The stent of claim 4, wherein the suture comprises a non-absorbable suture.

8. The stent of claim 4 wherein the suture comprises an absorbable suture.

9. The stent of claim 1, wherein the coating comprises a polymer made from monomers selected from the group consisting of lactide, glycolide, para-dioxanone, caprolactone, and trimethylene carbonate, caprolactone, blends thereof and copolymers thereof.

10. The stent of claim 1, wherein the polymer of the coating has a glass transition temperature above 55 C.

11. The stent of claim 1 wherein the polymer of the coating has a glass transition temperature above 120 C.

12. The stent of claim 1, wherein the polymeric coating comprise a polymer selected from the group consisting of polyacrylamides, polyethylene glycols, polyethylene oxide, vinyl alcohols, and poly(N-vinyl pyrrolidones).

13. The stent of claim 1, wherein the polymeric coating additionally comprises polyamide.

14. The stent of claim 9 wherein the coating comprises a melt polymer.

15. The stent of claim 9, wherein the coating comprises a solution polymer.

16. The stent of claim 9 wherein the filament comprises a surgical suture.

17. The stent of claim 12, wherein the suture comprises a monofilament.

18. The stent of claim 12, wherein the suture comprises a multifilament.

19. The stent of claim 12, wherein the suture comprises a non-absorbable suture.

20. The stent of claim 12 wherein the suture comprises an absorbable suture.

21. The stent of claim 1, wherein the coating comprises a polymer made from monomers selected from the group consisting of lactide, glycolide, para-dioxanone, caprolactone, and trimethylene carbonate, caprolactone, blends thereof and copolymers thereof.

22. The stent of claim 1, wherein the polymer of the coating has a glass transition temperature above 55 C.

23. The stent of claim 1 wherein the polymer of the coating has a glass transition temperature above 120 C.

24. The stent of claim 1, wherein the polymeric coating comprise a polymer selected from the group consisting of polyacrylamides, polyethylene glycols, polyethylene oxide, vinyl alochols, and poly(N-vinyl pyrrolidones.

25. The stent of claim 1, wherein the polymeric coating additionally comprises polyamide.

26. A method of maintaining a passageway of a body lumen substantially open, comprising the steps of:

providing a stent, said stent comprising:
    a helical structure having a plurality of coils, said structure having a longitudinal axis and a longitudinal passage, and said coils having a pitch, wherein said structure is made from a fiber, said fiber having a cross-section and said filament comprising:
        an elongated flexible, filament member, having an external surface and a cross-section; and,
        a polymeric outer coating on the surface of the member, wherein, the polymeric coating has sufficient mechanical integrity to effectively maintain the flexible member in a helical configuration; and, implanting said stent in a body lumen and maintaining the stent in the body lumen for a sufficient period of time to effectively maintain the passageway of the lumen substantially open for a desired period of time until the exterior coating softens, thereby converting the stent structure into a soft, flexible filamentary structure.

\* \* \* \* \*